(12) United States Patent
Kuhn et al.

(10) Patent No.: US 6,531,625 B2
(45) Date of Patent: Mar. 11, 2003

(54) CINNAMIC ESTERS

(75) Inventors: Walter Kuhn, Holzminden (DE); Gerhard Braun, Köln (DE); Stephan Klein, Bergisch Gladbach (DE)

(73) Assignee: Haarmann & Reimber GmbH, Holzminden (DE)

( * ) Notice: Subject to any disclaimer, the term of this patent is extended or adjusted under 35 U.S.C. 154(b) by 11 days.

(21) Appl. No.: 09/947,257

(22) Filed: Sep. 5, 2001

(65) Prior Publication Data

US 2002/0133038 A1 Sep. 19, 2002

(51) Int. Cl.$^7$ ............................................... C07C 69/76
(52) U.S. Cl. ........................................................ 560/104
(58) Field of Search ........................................ 560/104

(56) References Cited

U.S. PATENT DOCUMENTS

| | | | |
|---|---|---|---|
| 4,439,622 A | 3/1984 | Hansen et al. | 564/406 |
| 4,970,332 A | 11/1990 | Caskey | 560/104 |
| 5,359,122 A | 10/1994 | Huellmann et al. | 560/20 |
| 5,527,947 A | 6/1996 | Alexander et al. | 560/55 |
| 5,703,269 A | 12/1997 | Herrmann et al. | 560/19 |

FOREIGN PATENT DOCUMENTS

| | | |
|---|---|---|
| DE | 709 227 | 8/1941 |
| WO | 97/21659 | 6/1997 |

OTHER PUBLICATIONS

Ullmann's Encyclopedia of Industrial Chemistry, Sixth Edition, reprinted from vol. A 24, (month unavailable) 1999, pp. 231–239,Cinnamic Acid, Dorothea Garbe.

Ullmann's Encyclopedia of Industrial Chemistry, Fifth, Completely Revised Edition vol. A 7. (month unavailable) 1986 pp. 99–101, Cinnamic Acid, Dorethea Garbe.

Advanced Organic Chemistry, J. Marca 3$^{rd}$ edition. (month unavailable) 1985 pp. 220–221.

Tetrahedron Letters 40 (1999) (month unavailable) pp. 4815–4818, Application of a New Combination of Palladium and $CaC_3$ for an Aerobic Heck Reaction using Arenediazonium–Salts. Heiko Brunner, Naathalie Le Cousturier de Courcy and Jean–Pierre Genet.

Chem. Rev. (month unavailable) 1995, 95, pp. 537–538, Heterogeneous Basic Catalysis, Hideshi Hattori.

E. Dehmlow, A. Shamout: "Applications of Phase Transfer Catalysts. Part 16" Journal of Chemical Research. Synopses, 1981, Seite 106 XP008000993 London, GB ISSN: 0308–2342 Darstellung von Verbindung (5).

Terentiev. A B. et al Russian Chem. Bulletin (2000), 49(4) 722–723.*

Huang, Yaozeng et al, Tetrahedron Lett. (1986) 27(25), 2903–4.*

Takeda., T et al Synlett (1997), (10), 1149–1150.*

* cited by examiner

*Primary Examiner*—Paul J. Killos
(74) *Attorney, Agent, or Firm*—Joseph C. Gil; Noland J. Cheung

(57) ABSTRACT

In a novel process for the synthesis of cinnamic esters or substituted cinnamic esters, carboxylic esters are reacted, by condensation, with benzaldehyde or substituted benzaldehydes, respectively, in the presence of a solid with basic properties.

13 Claims, No Drawings

CINNAMIC ESTERS

FIELD OF THE INVENTION

The invention relates to a novel process for the synthesis of cinnamic esters or substituted cinnamic esters by condensation of carboxylic esters with benzaldehyde or substituted benzaldehydes, respectively, in the presence of a solid with basic properties.

BACKGROUND OF THE INVENTION

Cinnamic esters and substituted cinnamic esters are used, for example, as light protection filters in cosmetic applications and in plastics. 2-Ethylhexyl 4-methoxycinnamate is a light protection filter for the wavelength range of light from 280–315 nm (UV-B), which is known inter alia under the names NeoHeliopan® AV and OMC (Ullmanns Encyclopedia of Industrial Chemistry 6th Edition, Electronic Release, 1999, Vol. A 24, 231–239).

The synthesis of cinnamic esters or of 2-ethylhexyl 4-methoxycinnamate has hitherto been described in the following ways:

A) Condensation of benzaldehyde with acetic ester in the presence of alkali metal alkoxide (Ullmanns Encyclopedia of Industrial Chemistry 6th Edition, Electronic Release, 1999, Vol. A 24, 231–239).
B) Coupling of 4-halogenoanisol with acrylic ester catalyzed by palladium salts in the presence of suitable bases and phosphine ligands (Ullmanns Encyclopedia of Industrial Chemistry 5th Edition, 1986, Vol. A 7, 99–101, WO 90/10617, EP A 056491 and EP A 0719758).
C) Coupling of 4-methoxydiazonium salts with acrylic ester catalyzed by palladium in the presence of suitable bases (Genêt; Tetrahydron Letters 1999, 4815).
D) Addition of ketene onto acetals of benzaldehyde or substituted benzaldehydes (EP A 0490198).

A disadvantage of said processes is either the large amount of undesired salts which form during the synthesis, the use of noble metal catalysts, which are expensive and usually difficult to recover, and the use of toxic starting materials or laborious preliminary stages or subsequent steps.

SUMMARY OF THE INVENTION

An object of the present invention is a process for the synthesis of substituted cinnamic esters in which, in one reaction step, using suitable catalysts, benzaldehyde or substituted benzaldehydes are linked with acetic esters in a condensation reaction.

We have found a process for the preparation of cinnamic esters or substituted cinnamic esters of the general formula (I)

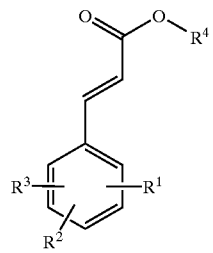

in which
$R^1$, $R^2$ and $R^3$ are identical or different and are hydrogen, alkoxy or alkyl, and
$R^4$ is alkyl,
which is characterized in that benzaldehydes (II) of the formula

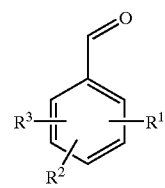

wherein
$R^1$, $R^2$, $R^3$ have the meanings given above,
are reacted with carboxylic esters (III)

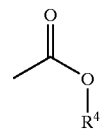

where
$R^4$ has the meaning given above
in the presence of a solid with basic properties.

DETAILED DESCRIPTION OF THE INVENTION

Surprisingly, the cinnamic esters can be prepared by the process according to the present invention in one step without salt contamination. In the general formulae I, II and III, the following general meanings apply: alkyl is a straight-chain or branched hydrocarbon radical having 1 to 16, preferably 1–10, carbon atoms, such as, for example, ethyl, methyl, propyl, iso-propyl, butyl, pentyl, hexyl, heptyl, octyl, 2-ethylhexyl, nonyl and decyl.

Alkoxy is a straight-chain or branched hydrocarbon radical, bonded via oxygen, having 1 to 6, preferably 1 to 3, carbon atoms, such as, for example, methoxy, ethoxy, propoxy, isopropoxy, butoxy, isobutoxy, pentoxy, isopentoxy, hexoxy or isohexoxy.

Examples of benzaldehydes which may be mentioned are: 4-methoxybenzaldehyde, 4-ethoxybenzaldehyde, 4-propoxybenzaldehyde, 4-iso-propoxybenzaldehyde, 4-butoxybenzaldehyde, 4-pentoxybenzaldehyde, 4-isopentoxybenzaldehyde, 4-methylbenzaldehyde, 4-ethylbenzaldehyde, 4-iso-propylbenzaldehyde, 4-propylbenzaldehyde, 4-butylbenzaldehyde.

Examples of carboxylic esters which may be mentioned are: hexyl acetate, heptyl acetate, octyl acetate, 2-ethylhexyl acetate, nonyl acetate, decyl acetate.

A preferred benzaldehyde (II) is 4-methoxybenzaldehyde, and a preferred carboxylic ester is 2-ethylhexyl acetate.

The molar ratio of benzaldehyde to carboxylic ester is generally in the range from 0.01 to 10, preferably in the range from 0.1 to 1 and most preferably, in the range from 0.2 to 0.5.

The process according to the present invention can be carried out in solvents or without diluent.

Solvents for the process according to the present invention are, for example, toluene, xylene, chlorobenzene, dichlorobenzene.

Water, which forms during the reaction is preferably removed according to the present invention from the reaction mixture, more preferably by distillation.

Entrainers for the water of reaction during the distillation which may be used are the solvents used or the carboxylic ester (III). The water can be separated off in a separator, it being possible to place the separator directly on the reactor or to use a separating column between reactor and separator. Water removal from the system is possible during reflux of the reaction solution or of the solvent.

Basic solids used for the process according to the present invention are metal carbonates and metal oxides, mixed oxides, mixtures of metal carbonates, mixtures of metal oxides and mixtures of metal carbonates and metal oxides. Preference is given to alkali metal and alkaline earth metal carbonates and oxides and, of these, the carbonates and oxides of sodium, caesium, potassium, magnesium and calcium. Aluminum oxide, zinc oxide and zirconium oxide may also be mentioned as basic solids.

A most preferred embodiment is potassium carbonate and caesium carbonate.

The basic solids can also be doped by sodium oxide, potassium fluoride, cerium oxide, ammonium fluoride, potassium carbonate and caesium carbonate.

The doping is preferably added in an amount of from 0.1 to 50% by weight, preferably in an amount of from 5 to 50% by weight, based on the total amount of the basic solid.

The solids can be used in pure form, supported or as a mixture, preference being given to mixtures of potassium carbonate and caesium carbonate, and more preference given to mixtures of caesium carbonate and potassium carbonate in which the two carbonates are used in equal parts by mass. The catalyst concentrations can be between 0.1 and 50% (w/w), preferred catalyst concentrations are between 5 and 50% (w/w). The catalyst can be thermally or mechanically pretreated prior to the reaction and can be used in powder form or as moldings.

Basic insoluble solids, specifically inorganic, basic, insoluble solids, are known per se as catalysts for condensation reactions of the aldol type (Chem. Rev., 1995, 95, 537–558, Catal. Today, 1997, 38, 321–337), where carbonyl compounds, such as aldehydes and ketones, are reacted with C—H-acidic compounds. A disadvantage of the described processes is the limitation to C—H-acidic compounds with C—H acidities which have an approximate pKa value (Advanced Organic Chemistry, J. March, 3rd Edition, 1985, 220–221) of less than 20. Processes for the preparation of cinnamic esters or substituted cinnamic esters by reacting acetic esters as C—H-acidic compound with benzaldehyde or substituted benzaldehydes are not described.

Inorganic solids, specifically oxides, with halogen-containing compounds, modified oxides, carbonates, mixtures of carbonates, mixtures of carbonates and oxides, characterized in that the substances have basic properties, are suitable catalysts for the synthesis of cinnamic esters or substituted cinnamic esters from benzaldehyde or substituted benzaldehydes, respectively, and acetic esters. This is surprising since inorganic solids are attributed with having a significantly lower basicity than, for example, alkali metal alkoxides, which are used in condensation reactions of the type described. The high activity and selectivity which is achieved with potassium carbonate and caesium carbonate in said reaction was particularly surprising. Moreover, an unexpected synergistic effect of potassium carbonate and caesium carbonate is found, i.e. the activity of the physical mixture of the two carbonates produces higher activities than the activities of the pure substances suggest.

The reaction pressure can be in the range from 0.1 to 10 bar, preferably in the range from 0.5 to 2 bar.

The reaction temperature is generally in the range from 100° C. to 300° C., preferably 150° C. to 250° C.

The reaction time can be between 0.5 and 48 h; preferred reaction times are between 0.5 and 5 h.

The reaction mixture must be thoroughly mixed during the reaction, which can take place by the boiling reaction solution alone and by the additional use of a stirrer. Isolation of the reaction product is carried out following removal of the catalyst by distillation under reduced pressure. The catalyst can be separated off by filtration and, in cases where the catalyst is water-soluble, by the addition of water, dissolution of the catalyst solid and subsequent phase separation.

The process according to the present invention can be represented by the following equation:

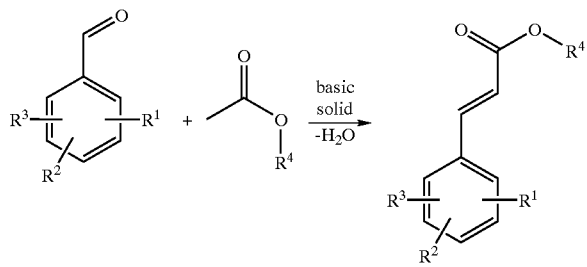

The process according to the present invention can be carried out, for example, as follows:

In general, 5–20% (w/w) of catalyst, which is either used without further pretreatment or prior to the reaction has been heated at elevated temperature or ground, are taken up in, for example, 2-ethylhexyl acetate and the reaction mixture is heated to the reflux temperature, then 4-methoxybenzaldehyde is added, the molar ratio of aldehyde to carboxylic ester being between 0.1 and 1. The progress of the reaction is ascertained by means of the water of reaction which forms and also by means of sampling and gas chromatographic analysis of the samples. When the reaction is complete, the catalyst is filtered off and the filtrate is distilled at subatmospheric pressure.

Using the present inventions it is possible to prepare cinnamic esters or substituted cinnamic esters by condensation of carboxylic esters with benzaldehyde or substituted benzaldehydes, respectively, catalyzed by a solid with basic properties with continuous removal of the water of reaction which forms.

Preferably, 2-ethylhexyl 4-methoxycinnamate can be prepared by the process according to the present invention.

The process according to the present invention for the synthesis of cinnamic esters and substituted cinnamic esters is easy to handle, can be carried out using low-cost and readily available starting materials, does not require toxic or ecologically unacceptable starting compounds, and has no byproducts apart from the water of reaction which forms, which avoids the inevitable formation of waste material. The process according to the present invention produces the target product in one synthesis step and uses a catalyst which can be removed easily from the product.

EXAMPLES

Example 1

A 250 ml glass reactor fitted with a stirrer, a distillation column (1 m in length), a water separator, a condenser and a dropping funnel is charged with 118 ml of 2-ethylhexyl acetate and 24 ml (bulk volume) of catalyst, and the mixture is heated to reflux temperature and then 27 g of 4-methoxybbenzaldehyde are quickly added. The progress of the reaction is monitored by sampling and via the corresponding amount of water of reaction. Conversions and yields are determined by means of gas chromatography using an internal standard. The catalysts are listed in Table 1 and the experimental results are summarized in Table 2.

TABLE 1

Catalysts.

| No. | Catalyst | Modification/doping | Pretreatment |
|---|---|---|---|
| 1 | MgO | | 500° C./2 h |
| 2 | MgO | modified with NaO | 500° C./2 h |
| 3 | Hydrotalcite/Kyowaad 300 | | 300° C./2 h |
| 4 | $K_2CO_3$ | | 500° C./2 h |
| 5 | $ZrO_2$ | | 500° C./2 h |
| 6 | $Al_2O_3$ | potassium fluoride | 500° C./2 h |
| 7 | $Al_2O_3$ | cerium oxide | 500° C./2 h |
| 8 | MgO | ammonium fluoride | 500° C./2 h |
| 9 | $Al_2O_3$ | $K_2CO_3$ (20% w/w) | 500° C./2 h |
| 10 | $K_2CO_3$ | $Cs_2CO_3$ (35% w/w) | 500° C./2 h |
| 11 | $Cs_2CO_3$ | | 500° C./2 h |
| 12 | $Al_2O_3$ | $Cs_2CO_3$ (20% w/w) | 500° C./2 h |
| 13 | Hydrotalcite/Kyowaad 300 from Kyowa | $Cs_2CO_3$ (20% w/w) | 500° C./2 h |
| 14 | MgO | $Cs_2CO_3$ (20% w/w) | 500° C./2 h |
| 15 | $SiO_2$ | $Cs_2CO_3$ (20% w/w) | 500° C./2 h |
| 16 | $Na_2CO_3$ | | 500° C./2 h |
| 17 | $(MgCO_3)*Mg(OH)_2*5H_2O$ | | 500° C./2 h |
| 18 | $CaCO_3$ | | 500° C./2 h |

TABLE 2

Experimental results.

| Catalyst | Reaction time [h] | 4-Methoxy-benzaldehyde conversion [%] | 2-Ethylhexyl 4-methoxy-cinnamate yield [%] |
|---|---|---|---|
| 1 | 6 | 54 | 15 |
| 2 | 22 | 83 | 17 |
| 3 | 22 | 82 | 9 |
| 4 | 8 | 67 | 52 |
| 5 | 8.5 | 27 | 0 |
| 6 | 8.5 | 89 | 62 |
| 7 | 8.5 | 28 | 0 |
| 8 | 22 | 90 | 10 |
| 9 | 22 | 58 | 40 |
| 10 | 1.5 | 98 | 82 |
| 11 | 2.5 | 95 | 85 |
| 12 | 22 | 82 | 22 |
| 13 | 22 | 100 | 55 |
| 14 | 22 | 97 | 29 |

TABLE 2-continued

Experimental results.

| Catalyst | Reaction time [h] | 4-Methoxy-benzaldehyde conversion [%] | 2-Ethylhexyl 4-methoxy-cinnamate yield [%] |
|---|---|---|---|
| 15 | 22 | 45 | 26 |
| 16 | 22 | 35 | 20 |
| 17 | 22 | 15 | 0 |
| 18 | 22 | 87 | 11 |

Example 2

Experiments with mixtures of caesium carbonate and potassium carbonate.

A 250 ml glass reactor fitted with a stirrer, a distillation column (1 m in length), a water separator, a condenser and a dropping funnel is charged with 118 ml of 2-ethylhexyl acetate and 24 ml (bulk volume) of catalyst, and the mixture is heated to reflux temperature and then 27 g of 4-methoxybenzaldehyde are quickly added. The progress of the reaction is monitored by sampling and via the corresponding amount of water of reaction. Conversions and yields are determined by means of gas chromatography using an internal standard. The catalysts and the experimental results are summarized in Table 3.

TABLE 3

Mixtures of potassium carbonate and caesium carbonate.

| Composition of the mixture of potassium carbonate and caesium carbonate [% w/w $K_2CO_3$/ % w/w $Cs_2CO_3$] | Reaction time [h] | 4-Methoxy-benzaldehyde conversion [%] | 2-Ethylhexyl 4-methoxy-cinnamate yield [%] |
|---|---|---|---|
| 0/100 | 3 | 100 | 87 |
| 25/75 | 2 | 97 | 86 |
| 50/50 | 1.2 | 99 | 91 |
| 65/35 | 1.5 | 96 | 85 |
| 87.5/12.5 | 2.5 | 99 | 90 |
| 95/5 | 3 | 96 | 91 |
| 99/1 | 3.2 | 96 | 85 |
| 100/0 | 8 | 67 | 52 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of cinnamic esters or substituted cinnamic esters of the general formula (I)

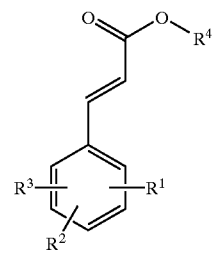

in which
R$^1$, R$^2$ and R$^3$ are identical or different and are hydrogen, alkoxy or alkyl, and
R$^4$ is alkyl
comprising the step of reacting benzaldehydes (II)

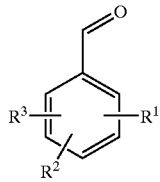

wherein
R$^1$, R$^2$, R$^3$ have the meanings given above,
with carboxylic esters (III)

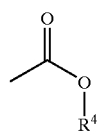

wherein
R$^4$ has the meaning given above
in the presence of a solid with basic properties.

2. A process according to claim 1, wherein the basic solids are oxides, oxides modified with halogen-containing compounds, carbonates, mixtures of carbonates, and mixtures of carbonates and oxides.

3. A process according to claim 1, wherein the basic solid has been heated at elevated temperature prior to the reaction.

4. A process according to claim 1, wherein the basic solids are potassium carbonate and caesium carbonate.

5. A process according to claim 1, wherein mixtures of caesium carbonate and potassium carbonate are used.

6. A process according to claim 5, wherein mixtures of caesium carbonate and potassium carbonate, in which both carbonates are employed in equal parts by mass, are used.

7. A process according to claim 1, wherein the water which forms during the reaction is removed from the reaction mixture during the reaction.

8. A process according to claim 1, wherein the reaction is carried out under reflux and the water of reaction which forms is removed from the reaction mixture during the reaction using an entrainer.

9. A process according to claim 8, wherein the entrainer is the carboxylic ester used as feed material.

10. A process according to claim 1, wherein the concentration of the basic solid is in the range from 1 to 50% (w/w), based on the total mass of the reaction mixture.

11. A process according to claim 1, wherein the molar ratio of the benzaldehyde used to the carboxylic ester is in the range from 0.01 to 10.

12. A process according to claim 1, wherein the basic solid is separated off by filtration.

13. A process according to claim 1, where the basic solid is water-soluble and the solid is dissolved by adding water and then the cinnamic ester or the substituted cinnamic ester is isolated by phase separation.

* * * * *